United States Patent [19]

Thelen et al.

[11] Patent Number: 4,912,271

[45] Date of Patent: Mar. 27, 1990

[54] PROCESS FOR THE MANUFACTURE OF VINYL CHLORIDE BY REACTION OF ACETYLENE WITH HYDROGEN CHLORIDE

[75] Inventors: Gerhard Thelen, Nottuln; Harald Bartels; Wilhelm Droste, both of Marl; Herbert Deppe, Borken, all of Fed. Rep. of Germany

[73] Assignee: Huels Aktiengesellschaft, Marl, Fed. Rep. of Germany

[21] Appl. No.: 339,721

[22] Filed: Apr. 18, 1989

[30] Foreign Application Priority Data

Apr. 30, 1988 [DE] Fed. Rep. of Germany ....... 3814785
Jul. 20, 1988 [DE] Fed. Rep. of Germany ....... 3824634

[51] Int. Cl.$^4$ ............................................. C07C 21/06
[52] U.S. Cl. .................................................. 570/233
[58] Field of Search ................................. 570/233, 250

[56] References Cited

U.S. PATENT DOCUMENTS 4,482,770 11/1984 Schmidhammer ................. 570/219

Primary Examiner—Howard T. Mars
Attorney, Agent, or Firm—Oblon, Spivak, McClelland, Maier & Neustadt

[57] ABSTRACT

Vinyl chloride is prepared by reacting acetylene with hydrogen chloride in the presence of a palladium compound catalyst in a solvent of an aliphatic and/or cycloaliphatic carboxylic acid amide at temperatures higher than room temperature.

12 Claims, No Drawings

PROCESS FOR THE MANUFACTURE OF VINYL CHLORIDE BY REACTION OF ACETYLENE WITH HYDROGEN CHLORIDE

BACKGROUND OF THE INVENTION

1. Field of the Invention:

The present invention relates to a process for the manufacture of vinyl chloride by the reaction of acetylene with hydrogen chloride.

2. Discussion of the Background:

The large-scale manufacture of vinyl chloride by the reaction of acetylene with hydrogen chloride is conventionally conducted in the gas phase in the presence of a heterogeneous $HgCl_2$-containing catalyst. For ecological reasons a substantial interest exists in employing a catalyst which is free of mercury chloride. However, alternative proposals for a gas phase process have failed to achieve success.

It is pointed out that some examples of the hydrochlorination of acetylene in the liquid phase are known and are described in the literature. These methods, however, are impracticable on a large scale. Thus, it is known, as described in U.S. Pat. Nos. 1,812,542; 1,934,324 and 3,113,158 that acetylene can be converted into vinyl chloride by reaction with aqueous hydrochloric acid in a reaction medium containing a dissolved copper compound, preferably dissolved copper chloride as a catalyst. In the process of U.S. Pat. No. 1,812,542 the catalyst solution in addition contains ammonium chloride, while the process described in U.S. Pat. No. 1,934,324 utilizes an alkali metal or alkaline earth metal chloride in the reaction medium. U.S. Pat. No. 3,113,158 describes a phosphine and/or diphosphine and/or methyl phosphine as present in the reaction medium.

Russian Patent No. 165,446 describes the hydrochlorination of acetylene in the presence of copper chloride in dimethylformamide as a solvent, while Russian Patent No. 232,956 describes the reaction as occurring in the presence of copper chloride in a triethanolamine solution acidified with hydrochloric acid.

The available literature describe acetylene conversions ranging from 26 to 99%. Space-time yields defined as $$\frac{\text{product (gram)}}{\text{catalyst volume (liter)} \cdot \text{time (hr)}}$$

of 10 to 130 g vinyl chloride/l·h are typically reported. Further, the high concentrations of up to 60% by weight of copper chloride in the solvent are high and are a disadvantage. Another drawback of the conventional catalyst systems is that they usually contain additional components.

Japanese Laid Open application 77/136,103 discloses a process for the manufacture of vinyl chloride from acetylene and hydrogen chloride in the presence of gold chloride and platinum chloride and/or palladium chloride as catalyst. Water or organic solvents such as paraffins, chlorinated hydrocarbons, diisopropylbenzene, chloralhydrate and ethylene chlorohydrin are used as solvents or suspending media. The catalytically active metal chloride can also be suspended on a carrier such as activated charcoal. The reference further discloses the use of a transition metal chloride as an additional catalyst component. Conversion of 54 to 74% with selectivities of about 99% are attained. The space-time yield amounts to about 100 g vinyl chloride/l·h. A drawback of the process described is that at least two different noble metal chlorides must be present and that only low conversion rates are attained. A need therefore continues to exist for an improved reaction system for the hydrochlorination of acetylene to vinyl chloride.

SUMMARY OF THE INVENTION

Accordingly, one object of this invention is to provide a method of manufacturing vinyl chloride by the hydrochlorination of acetylene in high space-time yields while simultaneously achieving high conversions and high selectivity in a homogeneous catalyst solution at low catalyst concentration in a simple manner.

Briefly, this object and other objects of the present invention as hereinafter will become more readily apparent can be attained in a method of preparing vinyl chloride by reacting acetylene with hydrogen chloride in the presence of a palladium compound catalyst in a solvent of an aliphatic and/or cycloaliphatic carboxylic acid amide at temperatures higher than room temperature.

DETAILED DESCRIPTION OF THE PREFERRED EMBODIMENTS

The present invention is a method of manufacturing vinyl chloride by the reaction of acetylene with hydrochloric acid in the presence of a noble metal catalyst in an organic solvent at temperatures above room temperature. An important aspect of the reaction is that a palladium compound is used as the catalyst in an aliphatic or cycloaliphatic carboxylic amide solvent.

Suitable palladium compounds as catalysts include, for example, palladium(II) chloride, alkali metal and alkaline earth metal tetrachloropalladates, e.g. $Na_2(PdCl_4)$, $K_2(PdCl_4)$, $Li_2(PdCl_4)$ and $(NH_4)_2(PdCl_4)$-hydrogen tetrachloropalladate (II), palladium (II) acetate, palladium acetylacetonate, bis(triphenylphosphine)palladium(II) chloride, bis(acetonitrile)palladium(II) chloride and bis(benzonitrile)palladium(II) chloride. Palladium(II) chloride is preferably employed as catalyst.

The reaction of acetylene with hydrogen chloride is carried out in the liquid phase in an aliphatic carboxylic acid amide serving as a solvent. The carboxylic acid amide may have a cyclic or acyclic structure and may be, for example:

(a) a carboxylic acid amide of the formula $R_1CONR_2R_3$, wherein $R_1$ and $R_2$ each is hydrogen or an alkyl moiety having 1 to 5 carbon atoms and $R_3$ represents an alkyl moiety having 1 to 5 carbon atoms such as for example formic acid ethylamide, acetic acid dimethyl amide, or (b) a carboxylic acid amide of the formula $R_1CONR_2R_3$, wherein $R_3$ represents hydrogen or an alkyl moiety having 1 to 5 carbon atoms and $R_1$ and $R_2$ together form a closed ring containing 2 to 5 carbon atoms, in particular of 3 to 4 carbon atoms. N-methylpyrrolidone is preferred as a solvent.

In order to ensure dissolution of the catalyst in the solvent, it is recommended to first enrich the solvent, optionally with heating, with hydrogen chloride, e.g. by passing hydrogen chloride gas into the liquid. Saturation of the solvent with hydrogen chloride is generally not necessary.

In the reaction of the invention acetylene and hydrogen chloride are reacted in relative amounts in a molar ratio of 1:1 to 1:3, preferably 1:1 to 1:1.5, with the reaction occurring in the presence of the catalyst. Based on the amount of solvent, the amount of catalyst employed is preferably an amount of 0.1 to 1.0% by weight, preferably 0.3 to 0.8% by weight.

Acetylene and hydrogen chloride are reacted at temperatures above room temperature. In any event, the temperature must be above the melting point of the hydrochloride of the carboxylic acid amide employed as solvent in the process. Preferably the reaction is carried out at a temperature of 100° C. to 200° C., preferably 140° C. to 170° C.

The two reactants acetylene and hydrogen chloride are introduced into the catalyst containing reaction solution simultaneously. Preferably the reactants are premixed, i.e. the reaction system is a bubble column. The conversion in this apparatus takes place at atmospheric pressure or slightly elevated pressure.

Other features of the invention will become apparent according to the following descriptions of the exemplary embodiments which are given for illustration of the invention and are not intended to be limiting thereof.

EXAMPLES

EXAMPLE 1

The reaction of acetylene with hydrochloric acid is carried out as follows:

A vertically standing double walled glass tube having an inner tube with an inner diameter of 2.2 cm is filled with a solution of 175 mg $Na_2PdCl_4$ in 45 ml N-methylpyrrolidone. Hydrogen chloride at a volumetric flow rate of 7.2 Nl/h (normliter/hour) and acetylene at a volumetric flow rate of 5.9 Nl/h are combined before entering the reactor and mixed and introduced into the catalyst solution kept at a temperature of 150° C. (Heat for the reaction is supplied by a heated fluid in the outer jacket.) The gaseous product mixture flowing from the reactor is analyzed gas chromatographically and the conversion of acetylene was 99.7% at a selectivity to vinyl chloride of 98.3%. The space-time yield amounts to 358 g vinyl chloride/l·h.

EXAMPLE 2

The reaction described in Example 1 was repeated in the presence of 150 mg $PdCl_2$ dissolved in 38 ml N,N-dimethylformamide at a temperature of 120° C. An acetylene conversion of 80% was obtained at a selectivity of 98.7%. These results were obtained when feeding 11.25 Nl/h acetylene and 11.25 Nl/h hydrogen chloride into the reactor. The space-time yield was 652 g vinyl chloride/l·h.

EXAMPLE 3

A 5.9 Nl/h amount of acetylene and 7.2 Nl/h hydrogen chloride were combined and passed into a reactor as described in Example 2. A conversion of acetylene of 94.7% and a selectivity of 98.9% to vinyl chloride were attained.

The space-time yield was 405 g vinyl chloride/l·h.

EXAMPLE 4

In a reaction conducted analogously to that of Example 1, a 96.0% conversion of acetylene and a selectivity of 98.8% to vinyl chloride were attained in the presence of 21 ml of N-methylpyrrolidone solution containing 4.7 g $PdCl_2$ per liter when a gas mixture of 13 Nl/h acetylene and 14.3 Nl/h hydrogen chloride were introduced into a reactor. The space-time yield was 1,638 g vinyl chloride/l·h.

EXAMPLE 5

The reaction described in Example 4 was conducted in the presence of 3 g $PdCl_2$/l at flow rates of 12.5 Nl/h acetylene and 15 Nl/h hydrogen chloride. The acetylene conversion was 89.5% and the selectivity to vinyl chloride was 98.7%. The space-time yield was 1,467 g vinylchloride/l·h.

EXAMPLE 6

In a manner analogous to that of Example 1, a reaction was conducted giving an acetylene conversion of 95.9%. The reaction was conducted in the presence of 30 ml N-methylpyrrolidone solution containing 4 g $PdCl_2$/l at a temperature of 148° C. and reactant feed rates of 13 Nl/h acetylene and 15.2 Nl/h hydrogen chloride. A selectivity to vinyl chloride of 99.2% and a space-time yield of 1,150 g vinylchloride/l·h were obtained.

EXAMPLE 7

A reaction was carried out in a manner analogous to that of Example 6 in the presence of 4.9 g $PdCl_2$/l. The acetylene conversion was 99.6%, the selectivity to vinyl chloride was 99.3% and the space-time conversion was 1,104 g vinyl chloride/l·h. The reaction was conducted at a temperature of 160° C. and 12 Nl/h acetylene and 14.4 Nl/h hydrogen chloride were fed to the reactor.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for the manufacture of vinyl chloride, comprising:
   reacting acetylene with hydrogen chloride in the presence of a palladium compound catalyst in a solvent of an aliphatic and/or cycloaliphatic carboxylic acid amide at temperatures higher than room temperature.

2. The process according to claim 1, wherein the catalyst is palladium(II) chloride.

3. The process according to claim 1, wherein the solvent is N-methylpyrrolidone.

4. The process according to claim 1, wherein from 0.1 to 1.0% by weight catalyst is employed based on the amount of solvent used.

5. The process according to claim 4, wherein said amount of catalyst ranges from 0.3 to 0.8 weight %.

6. The process according to claim 1, wherein said reaction occurs at a temperature of 100° to 200° C.

7. The process according to claim 6, wherein said reaction temperature ranges from 140° to 170° C.

8. The process according to claim 1, wherein acetylene and hydrogen chloride are reacted in a molar ratio of 1:1 to 1:3.

9. The process according to claim 8, said ratio ranges from 1:1 to 1:1.5.

10. The process according to claim 1, wherein said palladium compound is palladium(II) chloride, an alkali metal or alkaline earth metal tetrachloropalladate, hydrogen tetrachloropalladate(II), palladium(II) acetate, palladium acetylacetonate, bis(triphenylphosphine)palladium(II) chloride, bis(acetonitrile)palladium(II) chloride or bis(benzonitrile)palladium(II) chloride.

11. The process according to claim 1, wherein said carboxylic acid amide solvent has the formula $R_1CONR_2R_3$ wherein $R_1$ and $R_2$ are each hydrogen or a $C_{1-5}$ alkyl group or $R_1$ and $R_2$ together form a closed ring containing 2 to 5 carbon atoms and $R_3$ is $C_{1-5}$ alkyl.

12. The process according to claim 11, wherein in case of $R_1$ and $R_2$ together forming a closed ring containing 2 to 5 carbon atoms $R_3$ represents hydrogen.

* * * * *